(12) United States Patent
Habib

(10) Patent No.: US 6,694,984 B2
(45) Date of Patent: Feb. 24, 2004

(54) LIVER SURGERY

(75) Inventor: Nagy Adly Habib, London (GB)

(73) Assignee: Imperial College Innovations Limited (GB)

( * ) Notice: Subject to any disclaimer, the term of this patent is extended or adjusted under 35 U.S.C. 154(b) by 0 days.

(21) Appl. No.: 10/106,858

(22) Filed: Mar. 27, 2002

(65) Prior Publication Data
US 2002/0156511 A1 Oct. 24, 2002

(30) Foreign Application Priority Data
Mar. 27, 2001 (GB) .............................. 0107669

(51) Int. Cl.⁷ .............................. A61B 19/00
(52) U.S. Cl. .................... 128/898; 606/45; 606/49
(58) Field of Search ................. 606/32, 33, 41–42, 606/45, 48–50; 128/898; 607/101–102

(56) References Cited

U.S. PATENT DOCUMENTS

| | | | | |
|---|---|---|---|---|
| 4,469,098 A | * | 9/1984 | Davi ........................... | 606/7 |
| 5,190,541 A | * | 3/1993 | Abele et al. .................. | 606/46 |
| 5,582,588 A | * | 12/1996 | Sakurai et al. ................ | 604/22 |
| 6,071,281 A | * | 6/2000 | Burnside et al. .............. | 606/41 |
| 6,123,701 A | * | 9/2000 | Nezhat ........................ | 606/33 |
| 6,277,114 B1 | * | 8/2001 | Bullivant et al. ............. | 606/41 |
| 6,287,304 B1 | * | 9/2001 | Eggers et al. ................. | 606/37 |
| 6,443,952 B1 | * | 9/2002 | Mulier et al. ................. | 606/49 |
| 6,533,784 B2 | * | 3/2003 | Truckai et al. ................ | 606/50 |

\* cited by examiner

*Primary Examiner*—Roy D. Gibson
(74) *Attorney, Agent, or Firm*—Browdy and Neimark, P.L.L.C.

(57) ABSTRACT

Blood loss during solid organ surgery where diseased tissue is removed from the solid organ by delivery of thermal energy by one or more probes. The blood loss is stemmed by effecting coagulative necrosis of solid organ in the zone adjacent the probe(s). The or each probe can have means for cooling tissue in the vicinity of the tip of the probe. The method can be applied, inter alia, to liver and spleen surgery.

1 Claim, No Drawings

LIVER SURGERY

BACKGROUND OF THE INVENTION

The present invention is concerned with a technique for diminishing blood loss during solid organ surgery.

FIELD OF THE INVENTION

Because of their vascularity, solid organs pose particular problems concerning blood loss during surgery which need to be approached differently from blood loss problems when carrying out other types of surgery. The most important solid organs in this connection are the liver and the spleen.

Thus, blood loss, bile leak and postoperative liver function are the main concerns for surgeons operating on the liver (1), surgical resection remaining the only potentially curative procedure for dealing with hepatic tumours. Increased intraoperative bleeding is associated with higher postoperative complication and shorter long-term survival. In addition it is a major parameter in evaluating results of liver resection since it affects postoperative morbidity, mortality and long term survival in malignant disease. Operative blood loss can occur during dissection, parenchymal transection and revascularisation. Different techniques have been developed to allow safe liver resection (4–7). Surgeons can decrease intraoperative blood loss by limiting or occluding the inflow occlusion, performing a careful and sometime time-consuming parenchymal dissection or both. Inflow occlusion can be obtained by means of Pringle manoeuvre or total vascular exclusion. Parenchymal division can be performed using the scalpel, crushing the tissue with the finger or clamps, using ultrasonic dissectors and hydrodissectors or stapling devices. Vascular and biliary structures larger than 2 mm require ligation and division. However late bleeding and bile leak are possible even if high tech devices are used and are often caused by insufficient ligation or oozing from the resection surface secondary to tearing of small vessels.

Radio-Frequency-Thermal (RFT) energy has increasingly been used to locally ablate unresectable hepatic disease (8–11). Electricity converts current into thermal energy by ionic agitation and in so doing causes proteins to denature and results in coagulative necrosis.

Insofar as the spleen is concerned, it is one of the most vascular organs in the human body. It has a fine capsule structure with a soft parenchyma which bleeds profusely when injured. When the spleen starts to bleed because of accident or iatrogenic trauma during surgery in adults, it bleeds profusely and splenectomy is usually performed to arrest bleeding and to save life.

Partial splenectomy is not practised because of poor vascular control to induce haemostasis. Likewise Tru-cut biopsy of the spleen is never performed in the work-up diagnosis for haematological malignancies and often the surgeon is asked to perform a total splenectomy to provide the pathologist with splenic tissue to reach a diagnosis.

DESCRIPTION OF THE RELATED ART

Related disclosures are identified in a listing appended hereto and referred to by number in the foregoing passages and hereinafter.

OBJECT OF THE INVENTION

An object of the invention is to provide a technique for diminishing blood loss during solid organ surgery.

BRIEF SUMMARY OF THE INVENTION

According to the present invention, there is provided a method of reducing blood loss during solid organ surgery, wherein diseased or damaged tissue is removed from the solid organ by delivery of thermal energy to the tissue by a probe.

DESCRIPTION OF PREFERRED EMBODIMENT

A probe having a cooled tip has been found to be of use, provided that it can be employed with the cooling means inactivated during the withdrawal of the probe. As a result of the procedure of this invention, the region or regions of the solid organ through which the probe has been inserted is/are sealed. To obtain this effect over a wide area of tissue a plurality of probes will be required. These will advantageously be in line, linked in the form of a comb structure.

Although the method of this invention is described particularly with reference to use of a source of radio-frequency thermal energy for removal of diseased tissue, and will be described herein generally with reference thereto, the invention is not limited to the use of such heat source. Alternatively, it is possible to use other sources of heat deliverable by a probe such as laser energy source and bipolar energy source heat generating means, provided that one obtains coagulative dissection of the resection margins which can then be divided with a surgical scalpel.

In practice, the method defined above utilising RFT energy has been shown to define the edges of solid organ resection with an at least 2 cm wide coagulative necrosis zone in surgery using a multi probe application followed by a scalpel division of the parenchyma and suture of blood vessels bigger than about 2.5 mm. The technique can also be used in liver surgery, inter alia for major liver resections including right and left hemi-hepatectomies as well as in surgery carried out on the spleen.

Insofar as this invention offers a technique to control haemostatis in the spleen the method of this invention allows a surgeon to perform either partial splenectomy or Tru-cut biopsy. As with liver surgery, the rationale for vascular control preferably uses radiofrequency heat ablation (RFA) to induce coagulative desiccation of tissue, this resulting in complete obliteration of the vessel and ensuring haemostatis.

EXAMPLES

The following examples illustrate use of the technique embodied in the method of this invention.

Example 1

Four patients underwent RFT energy guided liver resection for hepatic malignant neoplasms. All patients underwent careful preoperative staging including spiral computed tomography and or magnetic resonance imaging showing no evidence of irresectable extra hepatic disease.

Under general anaesthesia a modified right subcostal incision was performed. The peritoneal cavity was examined for evidence of extra hepatic disease. Intra abdominal adhesion and falciform ligament were divided. The liver was then mobilized according to the size and the site of the lesion to be resected. An intraoperative ultrasonography was performed prior to the resection to locate the neoplasm. A line of parenchymal division was selected and scored on the peritoneum with electrocautery.

A newly-developed 'cooled-tip' needle and a 500 kHz-RF Generator (model RFG-3D—Radionics Europe, N.V., Wettdren, Belgium), which produces 100 W of power and allows measurements of the generator output, tissue impedance, and electrode tip temperature, was used to necrose the resection edges. The probe contains a 3 cm exposed electrode, a thermocouple just on the tip to monitor temperature and impedance and two coaxial cannulae through which chilled perfusate is circulated during RFT energy application to prevent tissue boiling and cavitation immediately adjacent to the needle.

In accordance with the characteristics of the resection to be performed a multiple probe application was required. To obtain a zone of necrosis with a 2.5 cm diameter, each application lasted about 8–12 minutes. The areas deepest and farthest from the liver surface were ablated first checking with the ultrasound the correct position of the probe. The areas of coagulative necrosis were monitored by the change in tissue impedance and the formation of micro-bubbles in the tissue detected by intraoperative ultrasonography. Pringle's manoeuvre was not applied. In accordance with the method of this invention, the saline circulation through the cannulae of the probe was stopped just prior to every probe removal. This achieved higher temperatures close to the electrode resulted in coagulation of the needle tract during withdrawal. Only when the surgeon was sure to have necrosed all the edges of the resection, division of the parenchyma was then performed with a scalpel. Compression of the cut surface of the liver stopped possible bleeding. Vascular and biliary structures larger than 2.5 mm were oversewn. A drain was placed at the site of resection and the abdomen was closed in layers.

All the procedures were completed as planned for each patient. None of the patients required blood transfusion. Postoperative mortality was 0%. The procedure was utilized in case of non-central lesions. Intraoperative blood loss and operating time were not significantly longer than that of a conventional liver resection and there were no complications related to the technique.

Example 2

RFA was carried out to perform both a bloodless partial splenectomy and a biopsy of the spleen. A 65 year old lady had developed a solitary metastasis 4 cm in diameter in the lower core of the spleen, having had previously an oöphorectomy and chemotherapy for ovarian carcinoma. Laparotomy confirmed the findings of CT scan. No other intra-abdominal or pelvic tumour recurrences were revealed.

The spleen was mobilised and the RFA needle probe of Example 1, with its 500 bite—RF Generator, was applied across the border between the lower core and the remaining unaffected spleen. RFA ablation proceeded 1 cm away from the tumour edge to create a corridor of coagulated tissue. Resection of the lesion was then performed with a surgical scalpel with zero blood loss. A Tru-cut biopsy of the remaining spleen was performed and sent for frozen section which showed the absence of any malignant cells. The RFA probe was placed inside the biopsy needle track to stop bleeding and induce coagulative vascular control. Haemostasis was excellent and the abdomen was closed without placing a surgical drain. The patient made a smooth post-operative recovery and was discharged. Post-operative splenic function prior to discharge a haematological was preserved.

This technique is believed to be the first report of controlled partial splenectormy and Tru-cut biopsy of the spleen. This technique could be performed using other sources of heat such as, laser microwave or bipolar energy. Further development of the technique allows a non operative percutaneous biopsy of the spleen.

Example 3

Between January 2001 and February 2002, 31 patients underwent RF assisted liver resection for hepatic tumours at the Hammersmith Hospital, London, UK. All patients underwent careful pre-operative assessment of their disease, including spiral computed tomography (CT) scan of chest and abdomen and/or magnetic resonance imaging (MRI), to exclude evidence of unresectable extra hepatic disease.

Under general anaesthesia, a modified right sub-costal incision was performed. The peritoneal cavity was examined for evidence of extra hepatic disease and an intra-operative ultrasonography (IOUS) was performed to reveal previously undetected lesions. The liver was then mobilised according to the size and site of the lesion to be excised.

Landmarks were drawn on the hepatic surface prior to resection. Two lines were made on the liver capsule with argon diathermy. A first or inner line marked the periphery of the tumour assisted by bi-manual palpation and IOUS. A second or outer line was drawn 2 cm away from the inner line to mark the site where the probe was to be positioned to achieve coagulative desiccation. Pringle's manoeuvre was not required.

Coagulative desiccation was performed along the outer line using the 'cooled-tip' RF probe and the 500 kHz-RF Generator used in Example 1.

The number of probe applications required to obtain a "zone of desiccation" was related to the thickness of the cut surface of the liver to be resected. Each application of RF energy took about 60 seconds to create a "zone of desiccation" in a core of tissue measuring 1 cm radius and 3 cm in depth.

Application of the RF energy began with the area deepest and farthest from the upper surface of the liver. The middle finger of the left hand was used to feel the tip of the probe piercing the capsule of the inferior surface of the liver while the right hand held the probe. The area of coagulative desiccation was monitored using IOUS which showed the change in tissue impedance and the formation of micro-bubbles in tissue.

Once the deepest 3 cm of tissue was coagulated, the probe was withdrawn by 3 cm to coagulate the next cylinder of tissue and so on until the upper surface of the liver was reached. Just prior to each probe removal the saline infusion was stopped to increase the temperature close to the electrode. This resulted in coagulation of the needle tract during withdrawal and reduced the possibility of bleeding from the probe tract and liver capsule. Once an area was coagulated, the probe was withdrawn completely and placed 1–2 cm away from the previous application. This allowed complete coagulation of a band of parenchyma extending along the second line.

The liver parenchyma was then divided using a scalpel. The plane of division was situated midway between the first and second line to leave a 1 cm resection margin away from the tumour and leave in situ 1 cm of coagulated surface.

After resection the "cool tip" probe was inserted into the cut surface in order to stop any remaining points of bleeding and to 'increase' the safety margin when required. A drain was placed at the site of resection. The abdomen was subsequently closed in layers. Following surgery all patients (except one with concomitant cardiac failure) were not transferred to ICU or high dependency unit (HDU), but were nursed on an open surgical ward.

In all patients, biochemical liver function tests were monitored before and after resection at 24 hrs and one week. All patients were followed up after surgery to record post-operative complications, tumour recurrence and survival. CT or MRI scans and carcinoembryonic (CEA) levels in patients with colorectal metasatases, were performed at months 1 and 3 and 6 monthly thereafter.

Results

The surgical resections carried out ranged from multiple metastasectomies to hemi-hapatectomies. Ten major resections (i.e. 3 segments or more according to Couinaud's classification) were performed: 7 right hepatectomies and 3 left hepatectomies. All the procedures were completed as planned. The median resection time was 47.5 mins (range 30–110). The median blood loss during resection was 30 mls (range 15–992) and mean pre-operative and postoperative haemoglobin values were 13.7 g/dL (SD$^\pm$1.68) and 11.79 g/dL (SD$^\pm$1.43) respectively. None of the patients required intra-operative blood transfusion. In one patient undergoing a right hepatectomy, probe positioning proved to be inadequate resulting in failure of coagulative desiccation of the right hepatic vein and blood loss of 992 mls. Two of the 31 patients required postoperative blood transfusion. In one case it was due to bleeding during mobilisation of the liver in a patient suffering from a carcinoid liver tumour which was previously embolised with collateral revascularisation. The recorded blood loss during actual resection in this patient was only 30 mls. The second patient received blood transfusion one week postoperatively. Following recovery 30 out of 31 patients were sent to the surgical ward. Only one patient was admitted electively to ICU due to concomitant heart failure. Another patient was nursed primarily in the surgical ward, but transferred to the ICU five days postoperatively due to an anastomotic leak from heptico-jejunostomy following left hepatectomy for hilar cholangiocarcinoma. This patient was the only patient that underwent re-operation, which was for refashioning of the biliary anastomosis. There were two postoperative complications in two patients who underwent high hepatectomy. One developed a subphrenic abscess that require percutaneous drainage, whilst the second developed a chest infection. Median postoperative stay for patients without complications was 8 days (range 5–10). Operative and hospital mortality was zero.

There was a significant change in liver function 24 hrs after resection when compared with pre-operative values, which did not completely normalise at one week. Although the follow-up period was short, there were no observed local tumour recurrences.

The results obtained in the foregoing examples have adduced certain observations. These are discussed generally, with respect to liver resections. However, as Example 2 shows the technique of the invention is effective in surgery carried out on solid organs other than the liver and specifically in spleen surgery.

Insofar as liver surgery, specifically is concerned, intra-operative blood loss is considered a negative prognostic factor after liver resection for primary or secondary neoplasm for morbidity and long term survival. Surgeons have tried to deal with it reducing the vascular inflow and improving the haemostasis of the cut edge using high tech devices as ultrasonic dissectors and hydrodissectors or lasers. Pringle' manoeuvre and total vascular exclusion are very useful in controlling intraoperative blood loss but produce an unavoidable isochaemic effect. Even though Huguet (12) showed how normal liver can tolerate complete ischaemia for more than 90', the liver is very sensitive to warm ischaemia. Consequently prolonged clamping can cause an increase of postoperative complication rate and can reduce the safety of resection in comparison to hepatectomy with inflow occlusion (7). The advent of ultrasonic dissectors and lasers allowed major resection to be performed without the need of vascular inflow or total exclusion with acceptable blood loss. However late bleeding and bile leak are possible even if high tech devices are used and are often caused by insufficient ligation or oozing from the resection surface secondary to tearing of small vessels.

The main advantages of RFT energy-facilitated liver resection are the avoidance of any inflow occlusion manoeuvre and the possibility to cut the liver easily and in a short time without significant bleeding. The limitations are the relative complexity of the procedure that requires extensive experience in using RFT energy and the time spent in necrosing resection limit.

RF energy converts current into heat. The high frequency current is delivered through an electrode placed in tissue which causes ionic agitation and consequently friction and tissue heating. The latter causes cellular dehydration resulting in coagulative desiccation, Many authors have reported series of RF tumour ablation for unresectable malignant tumours (8–10). The innovative step with our technique is that RF energy is applied to normal liver tissue surrounding the lesion to be excided to seal vascular and biliary structure along the plane of the resection. In contrast to coagulation of liver tumour tissue, coagulation of normal liver parenchyma is very fast. Each probe application induces desiccation in neoplastic tissue after about 20 minutes, but only 40–60 seconds are required to coagulate the same amount of normal liver tissue.

The duration of the transection time is dependent on the number of probe applications required to obtain a "zone of desiccation". This is related to the dimension of the cut surface after resection taking into account that each application of RF energy takes about 40–60 seconds to create a "zone of desiccation" in a core of tissue measuring 1 cm radius and 3 cm in depth. For example, a cylinder of tissue 12 cm in depth will require 4 applications, each application coagulating 3 cm of tissue which ill take about 4 minutes to produce. Using this novel technique the median resection time was 45 minutes (range 30–110).

When used carefully the surgeon can perform a virtually bloodless liver resection without inflow vascular occlusion. In particular, the entry point of each probe should be kept close to each other (i.e. 1 cm) to achieve some overlap of the coagulated areas to ensure that the coagulation has been complete. In one of the right hepatectomies there was failure of coagulative desiccation of the right hepatic vein. This was thought to be the result of the large volume of right liver parenchyma, making it difficult to achieve overlap of probe applications. Vascular control was achieved by placing the probe directly inside the open lumen of the right hepatic vein.

This technique offers significant advantages for both the patient and the surgeon. Liver resection becomes a less risky surgical procedure as systemic haemodynamic disturbances are reduced because liver blood flow is maintained during resection. In addition, the smaller surgical insult to the patient eliminates the need for ICU or HDU facilities and reduces postoperative mortality and general complications. Coagulative desiccation results in complete obliteration of the vessels and bile ducts at the resection margin. This leads to virtually 'zero' blood loss from the coagulated surface and eliminates the potential of post-operative bile leak from the resection margin. Another advantage of the technique, however, is that it is easy to teach. Surgeons with a good knowledge of liver anatomy can apply it to both segmental and major resections. Consequently 8 of the last 10 resections (5 of which were major resections) were performed by a surgical registrar.

In conclusion, the technique of the present invention simplifies hepatic parenchymal haemostasis and transection allowing a wider diffusion of liver surgery. Inflow occlusion is avoided and can result in decreased morbidity in patients with limited hepatic functional reserve.

However, there are obvious limitations to the technique. The first is that RF energy should not be applied continuously near the hilus or the vena cava because of fear of damaging these structures. The second is that it sacrifices parenchymal tissue that is usually spared using other resectional techniques. The latter limitation has been mitigated as the surgeon has greater vascular control with the technique allowing 'economical' small, local resections to be performed instead of large anatomical resections. Frequently the surgeon performs a right or left hepatectomy for localised tumours in order to follow anatomical lines to facilitate vascular control. This new technique will encourage the surgeon to perform more non-anatomical resections. Patients will benefit since more liver parenchyma can be spared.

REFERENCES

1) Bismuth H: Major hepatic resection under total vascular exclusion. Ann Surg 1989; 210:13–9
2) Brancatisano R, Isla A, Habib N. Is radical Hepatic surgery safe? Am J Surg 1998; 175: 161–163.
3) Fong Y, Cohen A M, Fortner J G, Enker W E, Turnbull A D, Coit D G, Marrero A M, Prasad M, Blumgart L H, Brennan M F. Liver resection for colorectal metastases. J. Clin Oncol 1997; 15: 938–946.
4) Hansen P D, Isla A M, Habib N A. Liver resection using total vascular exclusion, scalpel division of the parenchyma and a simple compression technique for haemostasis and biliary control. J Gastrointest Surg 1999; 3(5): 537–42.
5) Nuzzo G, Guiliante F. Giovianni I, et al. Hepatic resections in normothermic ischemia. Surgery 1996; 120: 852–58.
6) Tranberg K G, Rigotti P, Brackett K A, et al. Liver resection. A comparison using Nd-YAG laser, an ultrasonic surgical aspirator, or blunt dissection. Am J Surg 1986; 1951(3): 368–73.
7) Yamamoto Y, Ikai I, Kume M, et al. New technique for hepatic parenchymal resection using a cavitron ultrasonic surgical aspirator and bipolar cautery equipped with a channel for water dripping. World J Surg 1999; 23: 1032–37.
8) Curley S A, Izzo F, Delrio P, et al. Radiofrequency ablation of unresectable primary and metastatic hepatic malignancies: results in 123 patients. Ann Surg 1999; 230: 1–8.
9) Jiao L R, Hansen P D, Havlik R, et al. Clinical short-term results of radiofrequency ablation in primary and secondary liver tumours. Am J Surg 1999; 177: 303–206.
10) Gazelle G S, Goldberg S N, Solbiati L, Livraghi T. Tumor ablation with radiofrequency energy. Radiology 2000; 217(3): 633–46.
11) Cuschieri A, Braclen J, Boni L: (1999) Initial experience with laparoscopic ultrasound-guided radiofrequency thermal ablation of hepatic tumours. Endoscopy 31:318–321.
10) Huguet c, Gavelli A, Addario-Chieco P et al.: Liver ischemia for hepatic resection: where the limit? Surgery 1992;111:251–259

What is claimed is:

1. In a method of reducing blood loss during liver surgery, wherein diseased or damaged tissue is removed from the liver by delivery of thermal energy to the tissue by a probe, wherein the method is carried out to define liver resection with an at least 2 cm wide coagulative necrosis zone in surgery the improvement comprising: a multiprobe application followed by a scalpel division of the parenchyma and suture of blood vessels bigger than about 2.5 mm.

* * * * *